(12) United States Patent
Hillyer et al.

(10) Patent No.: US 9,480,786 B2
(45) Date of Patent: Nov. 1, 2016

(54) COMPONENT PREPARATION SYSTEM (71) Applicant: New York Blood Center, Inc., New York, NY (US)

(72) Inventors: Christopher D. Hillyer, New York, NY (US); Beth H. Shaz, New York, NY (US)

(73) Assignee: The New York Blood Center, Inc., New York, NY (US)

( * ) Notice: Subject to any disclaimer, the term of this patent is extended or adjusted under 35 U.S.C. 154(b) by 225 days.

(21) Appl. No.: 14/561,138

(22) Filed: Dec. 4, 2014

(65) Prior Publication Data

US 2015/0118109 A1    Apr. 30, 2015

Related U.S. Application Data (63) Continuation of application No. 13/291,822, filed on Nov. 8, 2011, now Pat. No. 8,920,659.

(60) Provisional application No. 61/411,107, filed on Nov. 8, 2010.

(51) Int. Cl.
| | | |
|---|---|---|
| *B01D 37/00* | (2006.01) | |
| *A61M 1/38* | (2006.01) | |
| *A61M 1/02* | (2006.01) | |

(52) U.S. Cl.
CPC .............. *A61M 1/38* (2013.01); *A61M 1/02* (2013.01); *A61M 1/0281* (2013.01); *A61M 2205/12* (2013.01); *A61M 2205/75* (2013.01)

(58) Field of Classification Search
CPC . A61M 1/02; A61M 1/0281; A61M 2205/12

USPC ...................................... 210/141, 257.1, 806
See application file for complete search history.

(56) References Cited

U.S. PATENT DOCUMENTS

| | | | |
|---|---|---|---|
| 5,281,342 | A | 1/1994 | Biesel et al. |
| 5,298,171 | A | 3/1994 | Biesel et al. |
| 5,795,483 | A | 8/1998 | Ung-Chhun et al. |
| 7,011,852 | B2 | 3/2006 | Sukavaneshvar et al. |
| 7,704,454 | B1 | 4/2010 | Langley et al. |

(Continued)

FOREIGN PATENT DOCUMENTS

JP        06-007432 A     1/1994

OTHER PUBLICATIONS

Pasqualetti D et al. "Blood component fractionation: manual versus automatic procedures." Transfusion and Apheresis Science 30:23-28, 2004.

(Continued)

*Primary Examiner* — Dirk Bass
(74) *Attorney, Agent, or Firm* — K&L Gates, LLP; Louis C. Cullman; Michelle Glasky Bergman (57) ABSTRACT

Disclosed herein are centrifuge-free self-contained systems for aseptically separating components of whole blood comprising at least one cassette for receiving whole blood; at least one red blood cell exclusion filter; at least one leukocyte reduction filters; at least one platelet exclusion filter; a plurality of product cassettes; and optionally a plurality of pumps and valves; and wherein the filters, pumps, valves, and cassettes are fluidly connected by tubing and the system does not include a centrifuge. Also disclosed are methods for obtaining blood components using the system.

8 Claims, 4 Drawing Sheets

(56) References Cited

U.S. PATENT DOCUMENTS

| | | |
|---|---|---|
| 7,708,889 B2 | 5/2010 | Hogberg et al. |
| 7,780,618 B2 | 8/2010 | Felt et al. |
| 8,920,659 B2 | 12/2014 | Hillyer et al. |
| 2006/0011545 A1 | 1/2006 | Latza |
| 2006/0180542 A1 | 8/2006 | Mari et al. |

OTHER PUBLICATIONS

International Search Report and Written Opinion of the International Search Authority for PCT/US2011/059799 issued May 29, 2012.

FIG. 4

COMPONENT PREPARATION SYSTEM

CROSS-REFERENCE TO RELATED APPLICATIONS

The present application is a continuation of U.S. patent application Ser. No. 13/291,822, filed Nov. 8, 2011, now U.S, Pat. No. 8,920,659,which claims the benefit under 35 U.S.C. §119(e) to U.S. Provisional Application 61/411,107 filed Nov. 8, 2010, the entire contents of all of which are incorporated by reference herein.

FIELD OF THE INVENTION

Disclosed herein are self-contained systems for processing whole blood into cellular and non-cellular components without the use of centrifugation and methods for preparing blood components using the system.

BACKGROUND OF THE INVENTION

Whole blood and its components, including erythrocytes (red blood cells, RBCs), platelets, and plasma, are used daily to treat persons with a wide range of clinical conditions ranging from acute trauma to genetic diseases. According to the Kalorama Information Report ("Blood, Blood Equipment Testing & Synthetic Blood Markets" 2008), the 2007 worldwide market for RBCs was 85 million units with a market value of $9.25 billion. The report forecasts the market to grow at a compound annual growth rate of 2.9% to 104.5 million units by 2014 with a market value of $11.3 billion. In 2007, the United States reported 14.46 million units of RBCs and 10.3 million units of platelets were transfused ("2007 Blood Collection & Utilization Survey", USDHHS). In order to maximize the utility of this relatively scarce resource and individualize for patient's needs, each unit of whole blood is separated into its components, each of which, after processing, is stored either in a rotator, refrigerator or freezer prior to transfusion. Each patient has unique needs for a specific component and thus blood is transfused as components rather than whole blood. Each component also has its ideal storage conditions. In the majority of blood centers or blood banks whole blood is collected from volunteer donors, the whole blood is then separated into the cellular and plasma components using manual separation techniques including pressure, centrifugation and/or filtration steps.

SUMMARY OF THE INVENTION

Disclosed herein is a self-contained component preparation system (CPS) that allows for whole blood to be processed into separate components without the use of centrifugation. The CPS uses a novel cassette-based flow-through system of specialized filters, solutions and product collection bags designed to maintain the integrity of the end products without the use of centrifugation.

In one embodiment disclosed herein, a centrifuge-free self-contained system for aseptically separating components of whole blood is provided comprising a cassette for receiving whole blood; at least one red blood cell exclusion filter; at least one leukocyte reduction filter; at least one platelet exclusion filter; a plurality of product cassettes; and wherein the filters and cassettes are fluidly connected by tubing and the system does not include a centrifuge.

In another embodiment, the centrifuge-free, self contained system further comprises at least one pump and/or at least one valve.

In one embodiment of the centrifuge-free self-contained system, the system comprises a first flow route wherein the cassette for receiving whole blood is fluidly connected to the red blood cell exclusion filter; the red blood cell exclusion filter is fluidly connected to a first pump; and the first pump is fluidly connected to a platelet rich plasma product cassette. In another embodiment, the platelet rich plasma product cassette is further fluidly connected to a platelet exclusion filter; the platelet exclusion filter is fluidly connected to a second pump; and the second pump is fluidly connected to a first plasma product cassette. In yet another embodiment, the first flow route further comprises a leukocyte-reduction filter disposed between the first pump and the platelet rich plasma product cassette. In another embodiment, the system further comprises a second flow route comprising a first preservative solution cassette fluidly connected to the first pump; a first leukocyte reduction filter fluidly connected to the red blood cell exclusion filter; and a leukocyte-reduced red blood cell product cassette fluidly connected to the first leukocyte reduction filter. In another embodiment, the system further comprises a third flow route comprising a second preservation solution cassette fluidly connected to the second pump; a second leukocyte reduction filter fluidly connected to the platelet exclusion filter and a platelet product cassette fluidly connected to the second leukocyte reduction filter.

In one embodiment of the centrifuge-free self-contained system, the system comprises a fourth flow route wherein the cassette for receiving whole blood is fluidly connected to the leukocyte reduction filter; the leukocyte reduction filter is fluidly connected to the red blood cell exclusion filter; the red blood cell exclusion filter is fluidly connected to a first gate; and the first pump is fluidly connected to a platelet rich plasma product cassette. In another embodiment, the platelet rich plasma product cassette is further fluidly connected to a platelet exclusion filter; the platelet exclusion filter is fluidly connected to a second pump; and the second pump is fluidly connected to a first plasma product cassette. In yet another embodiment, the system further comprises a fifth flow route comprising a first preservative solution cassette fluidly connected to the first pump; and a leukocyte-reduced red blood cell product cassette fluidly connected to the first pump. In still another embodiment, the system further comprises a sixth flow route comprising a second preservation solution cassette fluidly connected to the second pump; and a platelet product cassette fluidly connected to the second pump.

In one embodiment of the centrifuge-free self-contained system, the system comprises a seventh flow route wherein the cassette for receiving whole blood is fluidly connected to the leukocyte-reduction filter; the leukocyte-reduction filter is fluidly connected to at least one platelet exclusion filter in series; the platelet exclusion filter is fluidly connected to a leukocyte-reduced red blood cell reservoir cassette; the leukocyte-reduced red blood cell reservoir cassette is fluidly connected to a first gate; the first gate is fluidly connected to a pump; the pump is fluidly connected to a red blood cell exclusion filter; the red blood cell exclusion filter is fluidly connected to a second gate; and the second gate is fluidly connected to the leukocyte-reduced red blood cell reservoir cassette. In another embodiment, a reservoir cassette is disposed between the leukocyte-reduction filter and the first of the at least one platelet exclusion filter. In yet another embodiment, the system comprises less than three platelet exclusion filters. In another embodiment, each of the at least one platelet exclusion filters are further fluidly connected to both a platelet additive solution cassette and a platelet product cassette. In another embodiment, the first gate is further fluidly connected to a red blood cell product cassette. In another embodiment, the second gate is further fluidly connected to an erythrocyte storage solution cassette. In yet another embodiment, the red blood cell exclusion filter is further fluidly connected to a plasma product cassette.

In another embodiment of the centrifuge-free self-contained system, the system further comprises at least one source of vacuum pressure. In another embodiment, the system further comprises at least one sensor. In another embodiment, the system further comprises at least one processor.

In one embodiment disclosed herein, a method is provided of aseptically separating blood components in the absence of a centrifuge, comprising the steps of providing whole blood from a subject; connecting a bag containing the whole blood to a centrifuge-free self-contained system comprising: a cassette for receiving whole blood; at least one red blood cell exclusion filter; at least one leukocyte reduction filter; at least one platelet exclusion filter; a plurality of product cassettes; optionally at least one pump; optionally at least one valve; optionally at least one gate; and wherein the filters, cassettes, optional pumps, optional valves; and optional gates are fluidly connected by tubing and the system does not include a centrifuge; and obtaining at least one blood component selected from the group consisting of leukocyte-reduced red blood cells, platelets, red blood cells, and plasma from the whole blood.

In one embodiment disclosed herein, a centrifuge-free self-contained system for aseptically separating components of whole blood is provided, the system consisting essentially of a cassette for receiving whole blood; at least one red blood cell exclusion filter; at least one leukocyte reduction filter; at least one platelet exclusion filter; a plurality of product cassettes; optionally at least one pump; optionally at least one valve; and optionally at least one gate; wherein the filters, cassettes, optional pumps, optional valves, and optional gates are fluidly connected by tubing and the system does not include a centrifuge.

DETAILED DESCRIPTION OF THE INVENTION

Figure 1:
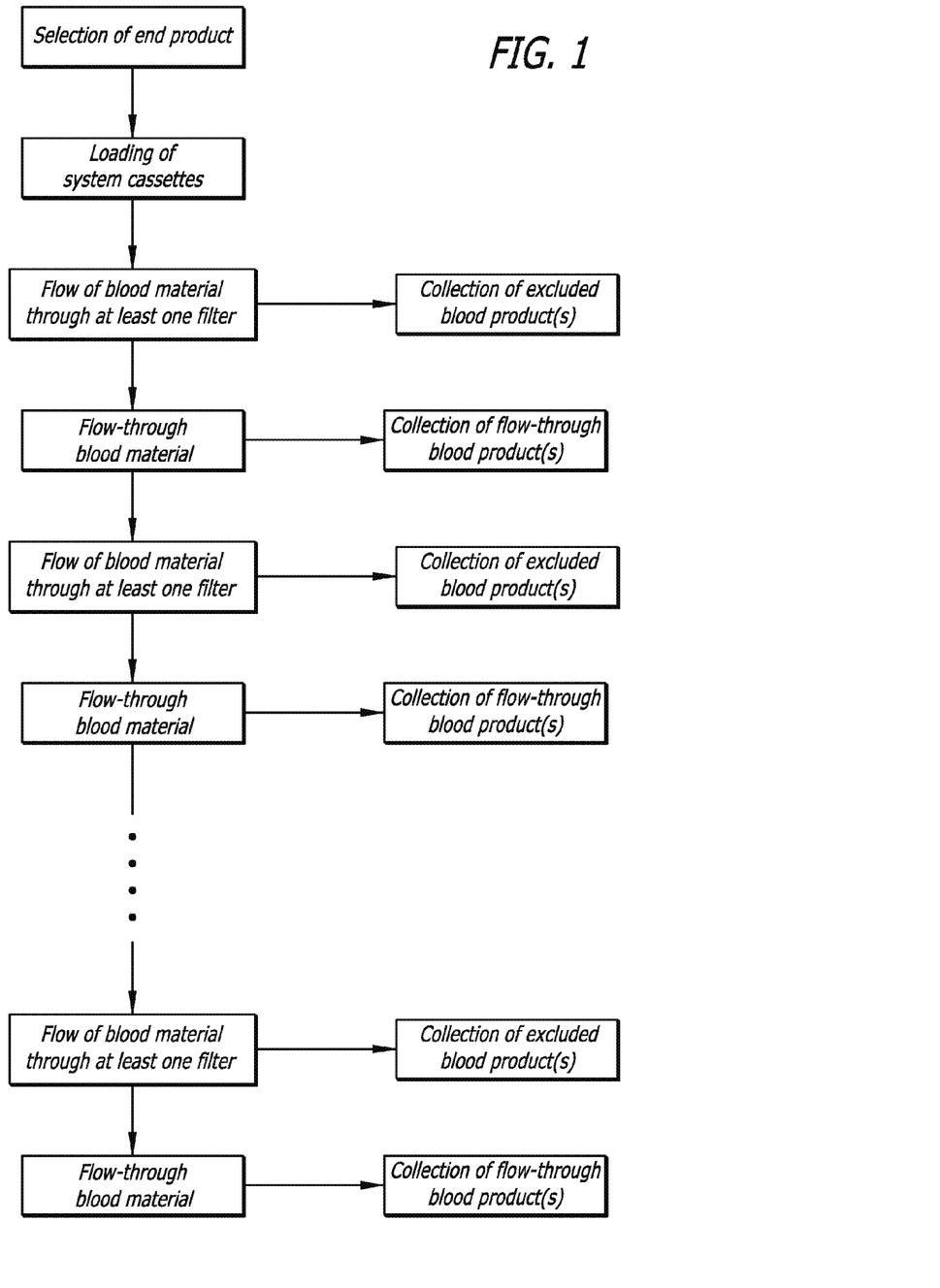
FIG. 1 depicts a flow diagram of the component preparation system described herein.

Disclosed herein is a self-contained component preparation system (CPS), and related methods of use. A schematic of the CPS and method is depicted in FIG. 1. The CPS aseptically separates the key components of whole blood into products suitable for transfusion. The CPS comprises a series of sterile articles (cassettes, filters, tubing, pumps, gates, and product bags) specific for a blood component to be separated from whole blood, or an intermediate product, without the use of centrifugal force to separate the blood components or exposure of the whole blood or blood components to the environment.

The CPS allows separation of blood components in a manner by which the viability of cells is preserved, such as to maintain their function, and exposure to environmental contamination, chemical agents, excessive centrifugal forces, and osmotic imbalances is minimized. Typically, contamination of blood products occurs when the blood is exposed to ambient air in the course of preparatory manipulations, chemical damage is possible when certain chemicals are used to lyse the accompanying red blood cells or to aggregate white cells, and physical damage follows the use of excessive centrifugal speed in separation of the cellular components of the blood according to their density, by centrifugal stratification.

The CPS does not use centrifugation to separate blood components and does not have a centrifuge component as part of the system. Use of centrifugation is injurious to red blood cells and platelets and increases the time required for separation of the blood components. Furthermore, the CPS limits exposure of the user (operator) to whole blood and thereby limits the risk of infection by blood-borne pathogens and other operational injuries to the user.

The CPS is initiated with a unit of whole blood, in the bag in which the blood was collected from the donor, which is connected to the system and the user (operator) selects the end products to be separated from the unit. A series of sterile closed system cassettes (bags) are loaded (connected) into the system. The choice of cassettes is based on which blood components are selected to be separated from the whole blood unit. The whole blood is obtained from blood donors through standard blood collection methods known to persons of ordinary skill in the art.

The CPS disclosed herein utilizes exclusionary filter technology that selectively excludes a particular component from the end product by either size or selective filtration. The blood or the separated component flows through the series of exclusionary filters and through operator-controlled "gates" that control the flow of blood material, depending on the components desired.

The gates can be manually set by the operator or via an automatic protocol. If the operator selects the option to recover the cellular components from the exclusionary filter, a product-specific preservative/nutrient solution can be passed through the exclusionary filter in a "reverse flow" manner thus eluting (or flushing) the captured components into a new product bag.

Following this procedure, the operator can produce one or more of the following blood components from the same unit of blood: leukocyte-depleted RBCs, platelet rich plasma (PRP), platelets, and plasma.

The system described herein does not use centrifugation thus allowing for a more efficient and rapid separation of the components. Furthermore, the closed system approach reduces the potential contamination of the components through extra manipulation. The ability to select the needed blood components allows blood centers to maximize the availability of specific components to meet patients' needs at any given time.

As used herein, "leukocyte-reduced RBCs" (LR-RBCs) refers to RBCs from whole blood that has been substantially depleted of white blood cells (WBC, leukocytes) by a method known to retain at least 85% of the original red blood cells and contain less than $5 \times 10^6$ residual leukocytes per unit. In certain embodiments, the LR-RBC component retains at least 90%, at least 92%, at least 95%, or at least 98% of the original red blood cells. In certain embodiments, the LR-RBC component contains less than $4 \times 10^6$, less than $3 \times 10^6$, less than $2 \times 10^6$, less than $1 \times 10^6$, or less than $5 \times 10^5$ residual leukocytes per unit. In additional embodiments, the LR-RBC component contains any combination of at least 85% of the original red blood cells and less than $5 \times 10^6$ residual leukocytes per unit disclosed herein.

As used herein, "platelet rich plasma" or "PRP" refers to a blood product comprising an increased concentration of platelets after removal RBCs and, optionally, WBCs. Platelet rich plasma is not completely free of WBCs or RBCs, however.

As used herein, "whole blood-derived platelets" refers to platelets that have been harvested from whole blood. These units may be pooled at up to 6 units of platelets into a single bag for transfusion. Whole blood-derived platelets can also be leukocyte-reduced and referred to as "leukocyte-reduced platelets." Whole blood-derived platelets are also referred to as random donor platelets (RDP) or as platelet concentrates.

As used herein, "plasma" refers to plasma isolated from whole blood which can be used directly or further processed into other plasma products. Plasma for transfusion can comprise one or more blood plasma preparations such as plasma frozen with 24 hours after phlebotomy (FP24), fresh frozen plasma (FFP), cryoprecipitate-reduced plasma and cryoprecipitate. Each of these plasma products has specific production requirements and regulations, as well as individualized storage and use specifications. The disclosed CPS produces plasma which can be further fractionated into one or more of these plasma preparations. The plasma produced from the disclosed system is FFP or FP24. FFP can be further fractionated into cryoprecipitate and cryoprecipitate-poor plasma. Plasma can also then be fractionated into plasma-derived products such as immunoglobulins (IVIG), albumin, factor VIII, etc. For the purposes of this disclosure, platelet rich plasma can also be used as plasma for transfusions.

As used herein, "fresh frozen plasma" refers to refers to the liquid portion of blood that has been frozen and preserved quickly (within eight hours) after a blood donation and will be used for transfusion. The term "FFP" is often used to mean any transfused plasma product. As used herein, the term FFP also refers to plasma frozen within 24 hours after phlebotomy and will be used for transfusion or further processing.

As used herein, "cryoprecipitate" refers to a frozen blood product prepared from FFP, also called "Cryoprecipitated Antihemophilic Factor", "Cryoprecipitated AHF", and most commonly just "cryo". Each unit typically contains a minimum of 80 IU of factor VIII, and 150 mg of fibrinogen. "Cryoprecipitate-reduced plasma" refers to the plasma that has been removed from the cryoprecipitate component.

All embodiments of the CPS disclosed herein comprise a series of articles (chambers, reservoirs, cassettes or bags, filters, tubing, gates, valves, ports, pumps, and vacuum sources) through which a unit of whole blood is processed into one or more of platelets, PRP, plasma, and LR-RBC. In one embodiment, the platelets are LR-whole blood-derived platelets. In another embodiment, both PRP and LR-RBC are produced. In another embodiment, plasma is produced. Each chamber, cassette, bag, filer, gate, pump, vacuum source, etc. may have a plurality of inlet ports and outlet ports. Each of these inlet and outlet ports can optionally have associated therewith a valve (or equivalent device) to regulate flow into or out from the article. These valves can be adjusted to stop flow of blood materials into or out of an article, to hold material in an article, or to cause material to enter and accumulate in an article.

Sterile component cassettes are designed to recover a particular blood component, and/or to provide sterile solution flow into the system, and/or to provide reservoirs for the collection and/or holding of intermediates in the component preparation process. The self-contained closed system maintains sterility of the components during isolation and storage and prior to transfusion. In one embodiment, the cassettes comprise bags, such as sterile blood collection bags known to persons of ordinary skill in the blood banking arts. In another embodiment, the cassettes are formed of at least one flexible and semi-rigid material such that the cassette has a variable volume. The cassettes further comprise at least one inlet port and at least one outlet port. The system also comprises tubing which is coupled to the inlet port or outlet port of a cassette and to other cassettes, gates or filters. The coupling mechanism is capable of disconnecting such that cassettes, filters and gates can be connected and disconnected aseptically.

The terms "inlet" and "outlet" with regard to ports refer to the direction of material flow in the system and each port can function as an "inlet" or "outlet". Furthermore the terms inlet, input and inflow can be used interchangeably with regard to ports. Even further, the terms outlet, output and outflow can be used interchangeably with regard to ports.

The term "port" refers to an opening, optionally associated with a valve, which allows connection between two articles of the system and flow of a material though the opening.

It will be understood by persons of ordinary skill in the art that each of the articles (chambers, reservoirs, cassettes or bags, filters, tubing, gates, valves, ports, pumps, and vacuum sources) is provided as sterile articles to create a sterile environment to allow for collection of sterile blood components. Each of the articles can be fabricated from sterile materials in a sterile environment prior to assembly, sterilized individually prior to assembly, or the whole system (prior to attachment of the whole blood bag) can be sterilized after assembly. The articles can be sterilized by one or a combination of methods including, but not limited to, radiation sterilization, ethylene oxide sterilization, and alcohol-based sterilization (flushing the article with an appropriate sterile alcohol-based solution). In some embodiments, the system is flushed with a sterile aqueous solution which does not contain an alcohol-based component prior to use.

Figure 2:
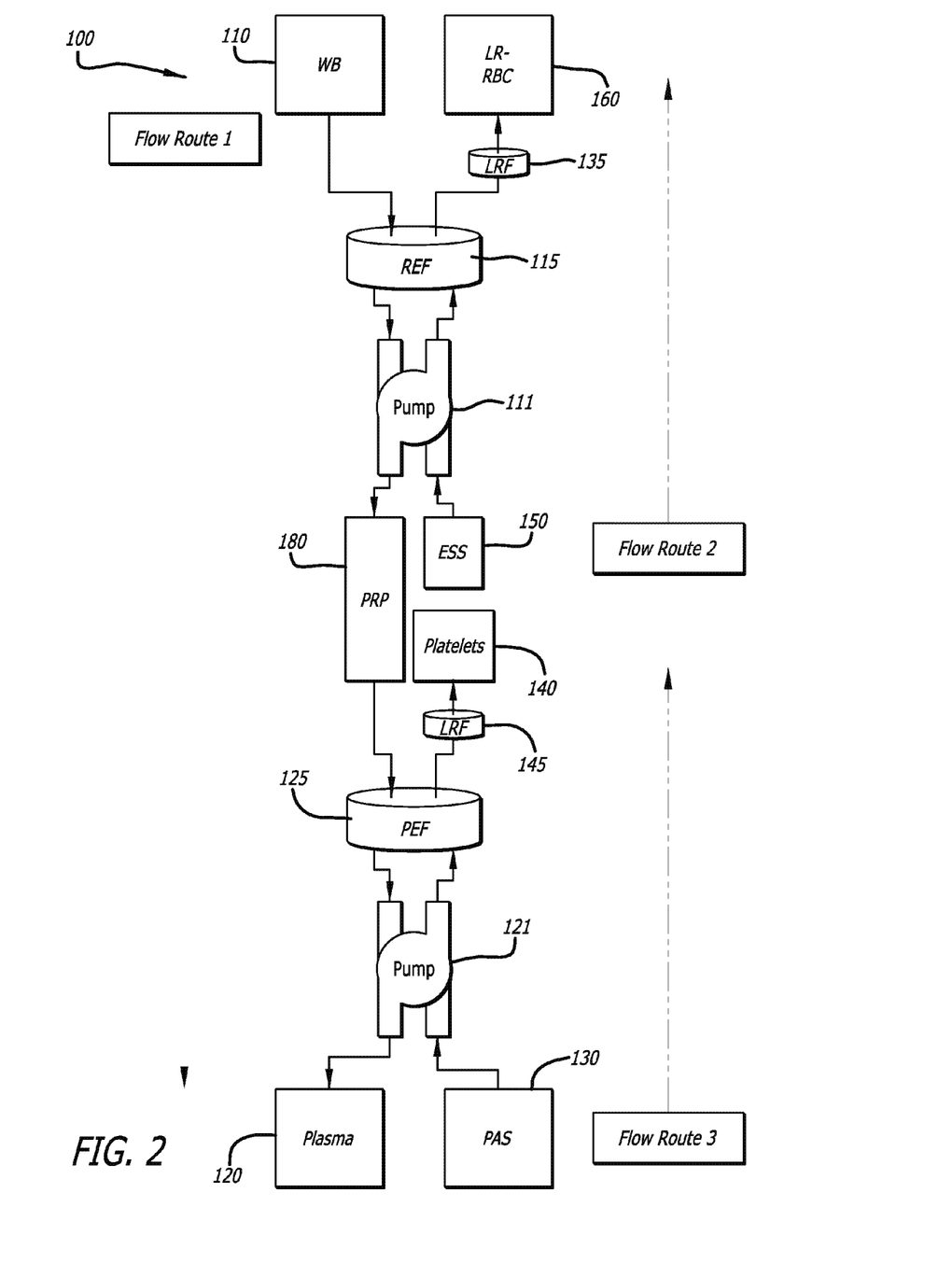
FIG. 2 depicts a flow diagram of one embodiment of the component preparation system described herein.

In one embodiment of the component preparation system depicted in FIG. 2 as CPS 100, flow route 1 comprises one unit of whole blood 110 from a single donor which is connected to tubing which passes through an RBC Exclusion Filter (REF) 115, which retains RBCs while allowing plasma, platelets and WBCs to pass through. The RBC-depleted blood passes through pump 111 which is set to allow the RBC-depleted blood to be collected as PRP in product cassette 180. The collection process can end at this point with the collection of the PRP product or the processing can continue.

The PRP passes through a Platelet Exclusion Filter (PEF) 125 that retains platelets and allows plasma to pass through pump 121, which allows the platelet-depleted plasma to be collected in plasma product cassette 120. The collection process can end at this point with the collection of the plasma product.

Flow route 2 encompasses the collection of LR-RBC from REF 115. A first preservative solution (such as an erythrocyte storage solution, ESS)-containing cassette 150 is attached to the system such that reversal of flow at pump 111 allows the first preservative solution to flow back across REF 115, thereby flushing RBCs trapped within REF 115 across a first leukocyte reduction filter (LRF1) 135 after which the leukocyte-reduced RBCs are collected in LR-RBC product cassette 160.

Optional flow route 3 encompasses the collection of platelets from PEF 125. A second preservative solution (such as platelet additive solution, PAS)-containing cassette 130 is attached to the system such that reversal of flow at pump 121 allows the second preservative solution to flow back across PEF 125, thereby flushing platelets trapped within PEF 125 across a second leukocyte reduction filter (LRF2) 145, after which the leukocyte-reduced platelet fraction is collected in RDP product cassette 140.

Alternatively, a LFR can be disposed between pump 111 and PRP product cassette 180 such that the PRP is leukocyte-reduced prior to collection.

Figure 3:
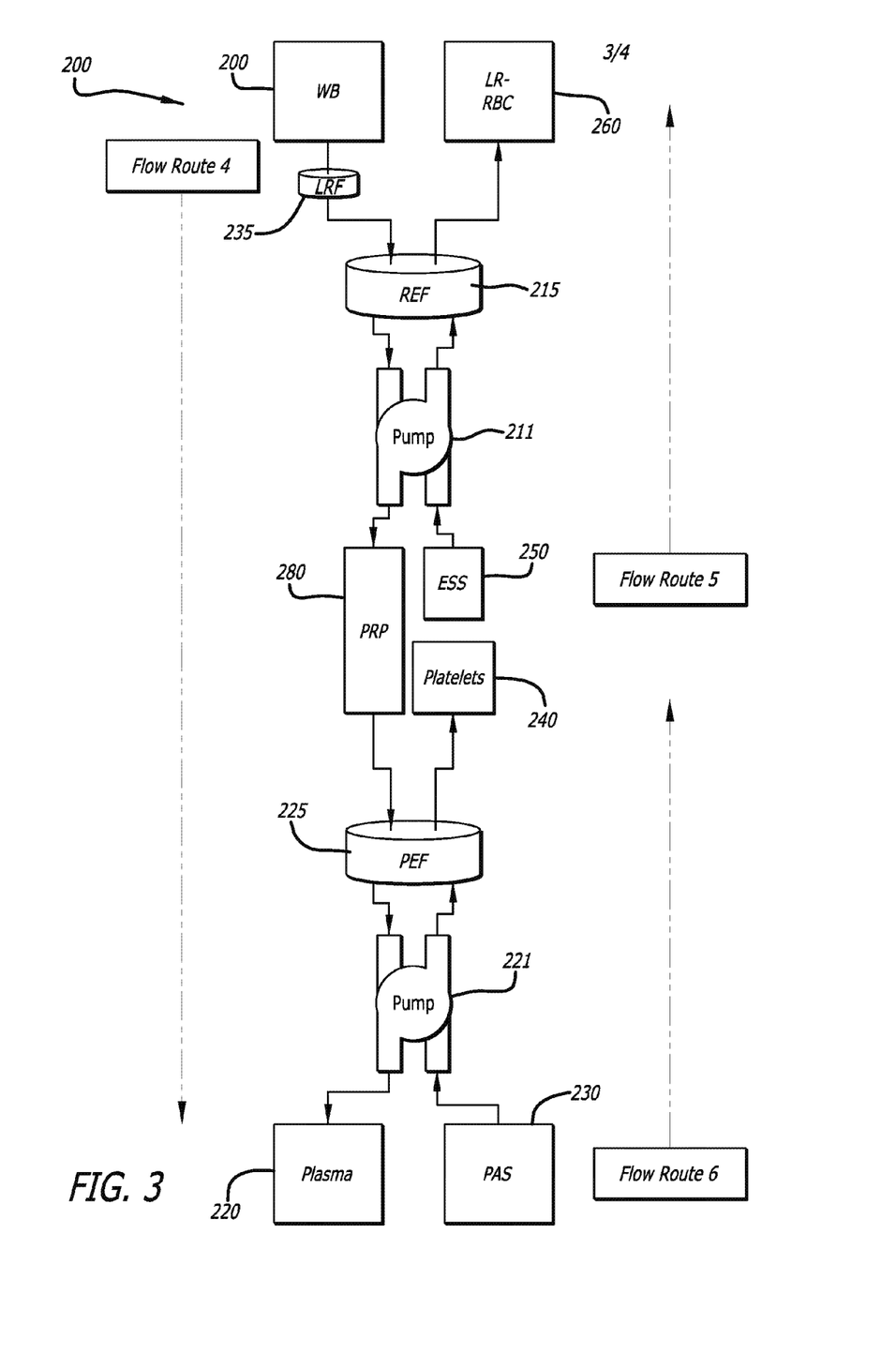
FIG. 3 depicts a flow diagram of a second embodiment of the component preparation system described herein.

In a second embodiment of the CPS, depicted in FIG. 3 as CPS 200, flow route 4 comprises one unit of whole blood 210 from a single donor which is connected to tubing which passes through LRF 235 and REF 215 in series. The leukocyte-reduced, RBC-depleted blood passes through pump 211 which allows the leukocyte- and RBC-depleted platelet rich plasma to be collected in PRP product cassette 280. The collection process can end at this point with the collection of the PRP product or the processing can continue.

If the processing continues, the PRP passes through PEF 225 which retains platelets and allows plasma to pass through pump 221 and collected in plasma product cassette 220. The collection process can end at this point with the collection of the plasma product.

Flow route 5 encompasses the collection of LR-RBC from REF 215. A first preservative solution (such as an ESS)-containing cassette 250 is attached to the system such that reversal of flow at pump 211 allows the first preservative solution to flow back across REF 215, thereby flushing leukocyte-reduced RBCs trapped within REF 215 into LR-RBC product cassette 260.

Optional flow route 6 encompasses the collection of platelets from PEF 225. A second preservative solution (such as a PAS)-containing cassette 230 is attached to the system such that reversal of flow at pump 221 allows the second preservative solution to flow back across PEF 225, thereby flushing platelets trapped within PEF 225 into RDP product cassette 240.

Figure 4:
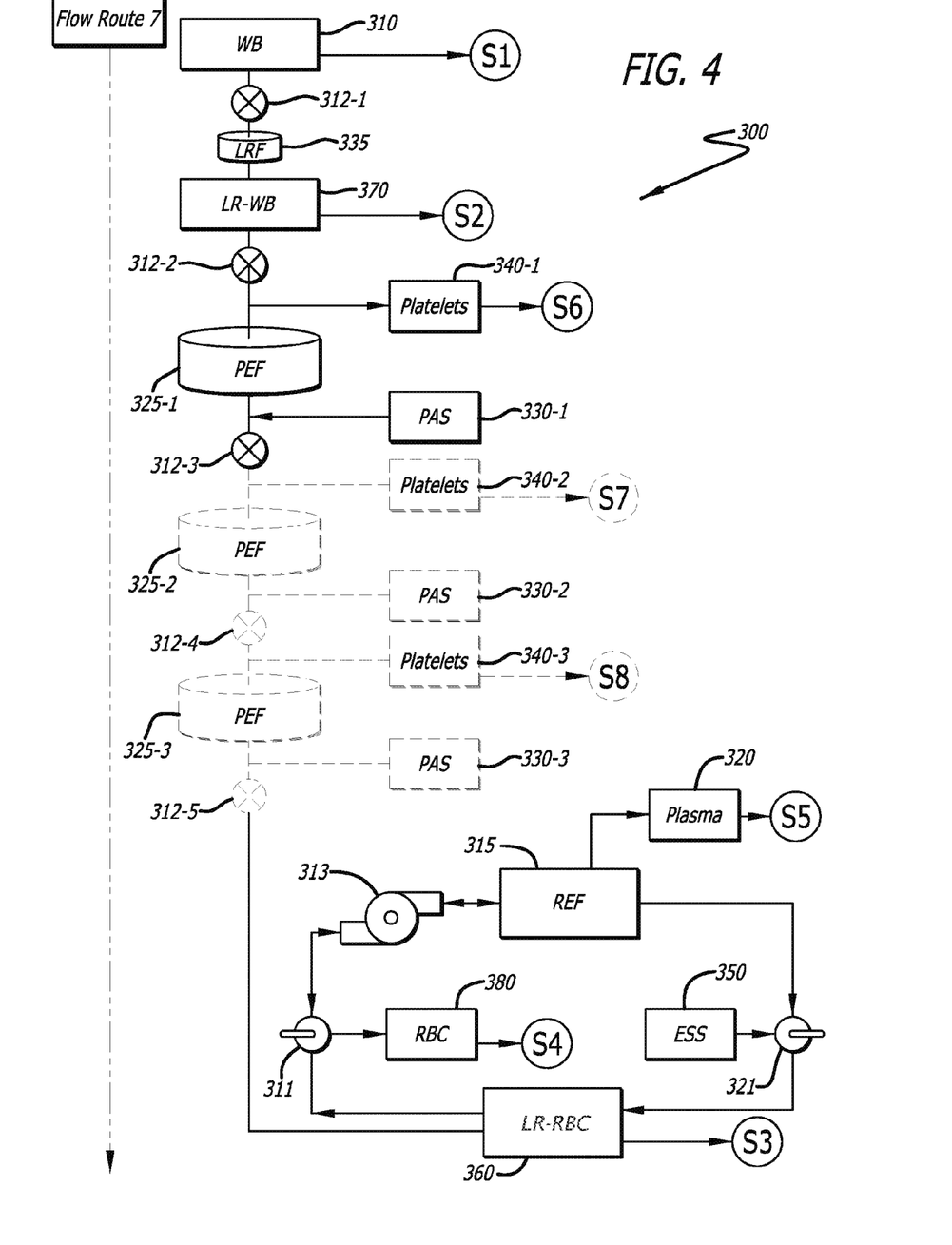
FIG. 4 depicts a flow diagram of a third embodiment of the component preparation system described herein.

In yet another embodiment of the CPS, depicted in FIG. 4 is CPS 300. Flow route 7 is initiated with one unit of whole blood 310 from a single donor which is connected to tubing which passes through LRF 335, retaining leukocytes in LRF 335, and the leukocyte-reduced blood exits LRF 335 and passes into a leukocyte-reduced whole blood (LR-WB) reservoir 370 before reaching at least one PEF 325. In some embodiments, up to three PEFs are linked in series, for example PEFs 325-1, 325-2 and 325-3 (FIG. 4). Each PEF 325 has one inlet port and one outlet port and leukocyte-reduced blood passes through PEF 325 from the inlet port to the outlet port. Adjacent to the inlet port is a diversion connected to a platelet product cassette 340 (340-1, 340-2 and/or 340-3 in some embodiments) and adjacent to the outlet port is a diversion connected to the PAS solution containing cassette 330 (330-1, 330-2 and/or 330/3 in some embodiments). Both diversions are controlled by valves disposed both before and after the PEFs 325 (valves 312-2, 312-3, 312-4 and 312-5). The valves can be closed and opened to control fluid flow from the whole blood through the series of PEFs and to control flow of PAS to flush platelets from the PEFs. As the platelets are retained by the filters, inlet and outlet tubing are closed with valves. The valves on the diverging tubes are opened to allow platelets to be released by flushing PEF 325 with PAS from cassette 330 (330-1, 330-2 and/or 330-3) to collect into platelet collection cassette 340 (340-1, 340-2 and/or 340-3).

In certain embodiments, LR-WB reservoir 370 contains a diluent, such as a capture solution, to dilute the blood material prior to entering PEF 325. Exemplary capture solutions include normal saline and PlasmaLyte, a sterile, nonpyrogenic isotonic solution.

Blood material moving through PRF 325 into LR-RBC reservoir 360 then passes through gate 311 and pump 313 into REF 315. REF 315 has at least three ports, at least one inlet port and at least two outlet ports. LR-RBC passing through pump 313 enter REF 315 though the inlet port and plasma is removed through a first outlet port into plasma collection cassette 320. The blood materials circulates through a loop comprising LR-RBC reservoir 360, gate 311, pump 313, REF 315, and gate 321 until all the plasma has been collected from the blood material.

After collecting plasma in the plasma cassette, the outlet port associated with plasma cassette 320 is closed. The REF 315 second outlet port allows red blood cells retained by REF 315 to be back flushed from REF 315 by flow of ESS from cassette 350 through gate 321 (reversal of flow) into REF 315. The RBCs are collected from REF 315 by reversing the direction of pump 313 and allowing the flushed RBCs to leave the REF 315 through the "inlet port", through gate 311 into RBC collection cassette 380.

CPS 300 also optionally contains vacuum and/or peristaltic pumps and vacuum sources to assist in the flow of materials through the system. In one embodiment, peristaltic pump 313 is disposed between gate 311 and REF 315 although additional pumps and/or vacuum sources disposed within the CPS are within the scope of the disclosed system.

In certain embodiments, samples are collected from reservoirs, collection cassettes and component bags of CPS 300 and are indicated in FIG. 4 as S1-S8.

In certain embodiments, the blood material circulates from LR-RBC bag 360 through gate 311 and pump 313 to REF 315, and through REF 315 and gate 321 back to LR-RBC bag 360 in a cycle until all plasma is removed from the blood material.

In certain embodiments, the flow is achieved and regulated through the use of one or more pumps and/or vacuum pressure sources to move the blood component material through the selected flow route(s). However, all pumps within the CPS depicted in FIGS. 2-4 are optional. In certain embodiments, movement of blood material through the system is controlled solely by the force of gravity. In other embodiments, only a single pump is included. Other embodiments include multiple pumps.

Vacuum pressure sources or pumps can be located at any position within the flow routes. In one embodiment, pumps 111, 121, 211, 221 and 313 are located at a location in the CPS to provide regulation of fluid flow. Addition of pumps and/or vacuum sources within a CPS are within the scope of the disclosed CPS. The CPS may also comprise pressure or flow sensors configured to measure pressure of flow of the blood components within the system, wherein the system may be configured to control the flow or pressure based on at the measurements by the sensor. In one embodiment the pump is a peristaltic pump.

As described above, the system comprises gates which control the direction of material flow within the system. In alternative embodiments, the gates are manual or automatic. In one embodiment, the gate comprises a valve. In another embodiment, the gate comprises a clamp. In another embodiment, the gate comprises an electronic switch controlled by a processor. In yet another embodiment, the gate is a multi-port stopcock. The disclosed gates can have two, three, four or more connection ports for connecting to two, three, four or more tubings, filters, ports, pumps, bags, or chambers. Each connection port of a gate can be opened or closed independent of any other connection port of the gate.

Filters, as used herein have inlet ports and outlet ports fluidly, aseptically, and removably connecting tubing to cassettes, bags, chambers, reservoirs, and/or gates. The filters used herein can take a variety of forms of porous medium, such as fibers combined together in a woven or unwoven form, loose fibers, foam, and/or one or more membranes, for example. The filter may be configured to retain one or more of leukocytes, platelets, and/or red blood cells. In one non-limiting example, the filter is a leukocyte reduction filter (LRF) configured to filter leukocytes from blood components such as, in a non-limiting example, RBCs or platelets, based in part on the size differential of blood particles. One non-limiting example of a LRF is the LRP6 leukoreduction filter marketed by the Pall Corporation of Glen Cove, N.Y. Another example is the Sepacell PLS-10A leukocyte reduction filter marketed by Baxter Healthcare Corp. of Deerfield, Ill. A further example is the IMUGARD filter marketed by Terumo of Japan. It should be understood that other known leukocyte reduction filters can be used with the CPS and that such filters are selected based on the specific separation conditions. In other embodiments, the filter is a red blood cell exclusion filter (REF) or a platelet exclusion filter (PEF). Exemplary suitable REF and PEF are available from the same commercial sources. Furthermore, the choice of filter is based on physical properties (such as size exclusion and/or ability to flush out retained components) and can comprise any commercially available filter with those properties. Therefore, for example, filters marketed as "leukocyte reduction filters" can be used as "platelet exclusion filters" or "red blood cell exclusion filters" or the contrary, as long as the filters fulfill the physical requirements of the system. Suitable red blood cell exclusion filter include tangential flow filters such as the CellFlo® filters available from Spectrum Laboratories, Inc.

A product-specific preservative/nutrient solution (PS) allows for elution of a cellular component from the filter without centrifugation. The PS is designed to allow for maximum storage of the separated blood components as required by national or local regulatory agencies. An exemplary PS is a platelet additive solution (PAS) such as InterSol™ (Fenwal Inc). Another exemplary PS is an erythrocyte storage solution (ESS), examples of which are know to persons of ordinary skill in the art.

Optionally, operation of the CPS is controlled by one or more processors included therein, and may comprise a plurality of embedded computer units to accommodate peripheral devices including but not limited to CD-ROM, modem, audio, networking and other capabilities. Furthermore, to assist the user control various aspects of the CPS operation, optionally included is a graphical interface.

In one embodiment, the processors control the function of the valves, pumps, and/or gates such that input by a user of the end product(s) to be separated results in the appropriate opening/closing of the gates and/or directional flow of fluid through the system.

The CPS according to any of the embodiments disclosed herein is configured as a portable desktop or bench top unit.

EXAMPLES

Example 1

Component Preparation System-FIG. 2

A whole blood donation is passed through the CPS of FIG. 2 as follows:
1. Whole blood is added to a whole blood bag.
2. Allow whole blood to pass through a REF, a gate, and a LRF and to collect PRP in a PRP product cassette.
3. Allow RBC-depleted blood to pass through a PEF and gate and collect plasma in a plasma cassette.
4. Collect LR-RBCs in a LR-RBC product cassette by flushing the REF with a preservative/nutrient solution from a solution cassette and passing the eluted RBCs through a leukocyte reduction filter before collecting in the LR-RBC product cassette.
5. Collect platelets in a platelet product cassette by flushing the PEF with a preservative/nutrient solution from a solution cassette and passing the eluted platelets through a leukocyte reduction filter before collecting the platelets in the platelet product cassette.

Example 2

Component Preparation System-FIG. 3

A whole blood donation is passed through the CPS of FIG. 3 as follows:
1. Whole blood is added to a whole blood bag.
2. Allow whole blood to pass through a LRF and an REF before passing through a gate to collect PRP in a PRP product cassette.
3. Allow RBC- and leukocyte-depleted PRP to pass through a PEF and gate and collect plasma in a plasma cassette.
4. Collect LR-RBCs in a LR-RBC product cassette by flushing the REF with a preservative/nutrient solution from a solution cassette and passing the eluted RBCs to a LR-RBC product cassette.
5. Collect platelets in a platelet product cassette by flushing the PEF with a preservative/nutrient solution from a solution cassette and passing the eluted platelets to a platelet product cassette.

Example 3

Component Preparation System-FIG. 4

A whole blood donation was passed through the CPS of FIG. 4 as follows:
1. 150 ml of whole blood was added to cassette 310
2. Added 30 ml of capture solution to reservoir 370 and cassette 310, reservoir 370, LRF 335 and PEF 325 components were connected vertically as depicted in FIG. 4.
3. Collected 10 ml sample of initial whole blood unit as sample S1.
4. Allowed whole blood to pass through LRF 335 and collect in cassette 370.
5. Mixed the leukoreduced blood with the capture solution in cassette 370 and collected 10 ml sample as sample S2.
6. Allowed leukoreduced blood to pass through PEFs 325-1, 325-2, and 325-3 and collected platelet-reduced blood in reservoir 360.
7. Collected sample S3 from reservoir 360.

8. Initiated reverse flow across PEFs 325-1, 325-2, and 325-3.

9. Allowed solution to flow from PAS reservoirs 330-1, 330-2, and 330-3 across PEFs 325-1, 325-2 and 325-3, and collected platelets in RDP cassettes 340-1, 340-2, and 340-3.

10. Collected samples S6, S7, and S8 from RDP cassettes 340-1, 340-2, and 340-3, respectively.

11. Allowed forward movement of peristaltic pump 313 to move blood material from reservoir 360 to REF 315.

12. Collected permeate (plasma) in plasma collection cassette 320 and allowed blood material flow from second outlet port of REF 315 back to reservoir 360.

13. Repeated steps 11 and 12 until the permeate plasma was completely separated from the red blood cells.

14. Collected sample S5 from plasma collection cassette 320.

15. Closed outlet port to plasma cassette 320, reversed pump 313 and configured gate 321 such that ESS solution flowed from ESS cassette 350 through gate 321 and into REF 315.

16. Configured gate 311 such that red blood cells were flushed from REF 315 and passed through gate 311 into RBC cassette 380.

17. Collected sample S4 from RBC cassette 380.

All sample collection actions are for experimental system validation purposes only and are not part of the CPS. The samples were transferred to EDTA-containing tubes for hematology analysis to obtain complete blood counts at each step of the CPS (Tables 1 and 2). The results were confirmed by flow cytometry. Platelet numbers were determined by flow cytometry.

Thus, the CPS is suitable to produce purified populations of blood cells and components from whole blood in a sterile, self-contained process. In this study, the leukocyte reduction filter excluded most of the platelets and therefore only few platelets were recovered from the PEFs. Substitution of the LRF (using another LRF which does not exclude platelets) will allow the platelets to pass through the LRF filter to be retained in the PEFs as shown in Example 4.

Example 4

Analysis of Platelet Exclusion Filters

Platelet retention from the system was re-evaluated as platelets were captured by the leukocyte reduction filter during whole blood component separation in Example 3.

A 100 ml platelet sample was connected to a first PEF and a second PEF in series. Excluded platelets were flushed from each filter using a preservative solution. The number of platelets was determined in the initial sample (B1), in the filtrate after passage through both PEFs (B4), the backflush from the first PEF (B2), and backflush from the second PEF (B3) (Table 3).

TABLE 1

Hematology analysis

| Sample | WBC | RDW-SD | RBC | RDW-CV | HGB | HCT | MPV | MCV | MCH | MCHC | PLT |
|---|---|---|---|---|---|---|---|---|---|---|---|
| S1 | 3.19 | 40.00 | 3.52 | 13.10 | 9.30 | 29.5 | 9.3 | 83.8 | 26.4 | 31.5 | 266 |
| S2 | 1.00 | 52.70 | 2.23 | 15.30 | 5.80 | 21.1 | — | 94.6 | 26.0 | 27.5 | |
| S3 | 0.00 | 43.00 | 1.75 | 13.70 | 4.60 | 14.9 | — | 85.1 | 26.3 | 30.9 | |
| S4 | 0.01 | | 0.40 | | 1.10 | 4.1 | | 102.5 | 27.5 | 26.8 | 21 |
| S5 | 0.03 | | 0.00 | | 1.11 | 0.0 | | — | — | — | 1 |
| S6 | 0.01 | 54.00 | 0.74 | 16.50 | 1.9 | 6.9 | — | 93.2 | 25.7 | 27.5 | 7* |
| S7 | 0.08 | 57.30 | 0.33 | 17.6 | 0.9 | 2.9 | | 93.9* | 27.3 | 29.0 | 3 |
| S8 | 0.01 | 54.8 | 0.31 | 17.4 | 0.9 | 2.9 | — | 93.5 | 29.0* | 31.0* | 4* |

WBC = WBC count ($\times 10^3/mm^3$); RDW-SD = RBC distribution width size difference; RBC = RBC count ($\times 10^6/mm^3$); RDW-CV = RGB distribution width - mean corpuscular volume (%); HGB = hemoglobin (g/dL); HCT = hematocrit (%); MPV = mean platelet volume (fL); MCV = mean corpuscular volume (fL); MCH = mean corpuscular hemoglobin (pg/cell); MCHC = mean corpuscular hemoglobin concentration (g/dL); PLT = platelet count ($\times 10^3/mm^3$); — no value obtained.

TABLE 2

Cell counts

| Sample (per volume) | Platelets ($\times 10^9$) | RBCs ($\times 10^{11}$) | WBCs ($\times 10^8$) | Hemoglobin (g/dl) |
|---|---|---|---|---|
| S1 (150 ml) | 39 | 5.28 | 4.7 | 9.3 |
| S2 (150 ml) | 1.7 | 3.34 | 0 | 5.8 |
| S3 (150 ml) | — | 2.62 | 0 | 4.6 |
| S4 (300 ml) | 1.36 | 0.53 | 0 | 1.1 |
| S5 (50 ml) | 0 | 0 | 0 | 1.1 |
| S6 (50 ml) | 0.2 | 0.15 | 0 | 1.9 |
| S7 (50 ml) | 0.15 | 0.16 | 0 | 0.9 |
| S8 (50 ml) | 0.15 | 0.37 | 0 | 0.9 |

TABLE 3

Platelet counts

| Sample (per 100 ml) | Platelet Count ($\times 10^9$) |
|---|---|
| B1 | 70 |
| B2 | 30 |
| B3 | 4.9 |
| B4 | 3.1 |

As can be seen from Table 3, an acceptable recovery of platelets is obtained from the first PEF and the filtrate (B4) is substantially depleted of platelets.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A centrifuge-free self-contained system for aseptically separating components of whole blood comprising:
   a cassette for receiving whole blood;
   at least one red blood cell exclusion filter;
   at least one leukocyte reduction filter;
   at least one platelet exclusion filter;
   a plurality of product cassettes;
   wherein the filters and cassettes are fluidly connected by tubing and the system does not include a centrifuge; and
   wherein the system comprises a flow route wherein the cassette for receiving whole blood is fluidly connected to the leukocyte-reduction filter; the leukocyte-reduction filter is fluidly connected to at least one platelet exclusion filter in series; the platelet exclusion filter is fluidly connected to a leukocyte-reduced red blood cell reservoir cassette; the leukocyte-reduced red blood cell reservoir cassette is fluidly connected to a first gate; the first gate is fluidly connected to a pump; the pump is fluidly connected to a red blood cell exclusion filter; the red blood cell exclusion filter is fluidly connected to a second gate; and the second gate is fluidly connected to the leukocyte-reduced red blood cell reservoir cassette.

2. The centrifuge-free self-contained system of claim 1, wherein a reservoir cassette is disposed between the leukocyte-reduction filter and the first of the at least one platelet exclusion filter.

3. The centrifuge-free self-contained system of claim 1, comprising less than three platelet exclusion filters.

4. The centrifuge-free self-contained system of claim 1, wherein each of the at least one platelet exclusion filters are further fluidly connected to both a platelet additive solution cassette and a platelet product cassette.

5. The centrifuge-free self-contained system of claim 1, wherein the first gate is further fluidly connected to a red blood cell product cassette.

6. The centrifuge-free self-contained system of claim 1, wherein the second gate is further fluidly connected to an erythrocyte storage solution cassette.

7. The centrifuge-free self-contained system of claim 1, wherein the red blood cell exclusion filter is further fluidly connected to a plasma product cassette.

8. A method of aseptically separating blood components in the absence of a centrifuge, comprising the steps of:
   providing whole blood from a subject;
   connecting a bag containing the whole blood to the centrifuge-free self-contained system as recited in claim 1;

and obtaining at least one blood component selected from the group consisting of leukocyte-reduced red blood cells, platelets, red blood cells, and plasma from the whole blood.

* * * * *